United States Patent
Bortolai et al.

(10) Patent No.: US 9,861,571 B2
(45) Date of Patent: Jan. 9, 2018

(54) SOAP BAR FORMULATIONS WITH IMPROVED SKIN SOFTNESS COMPRISING NONIONIC POLYMER STRUCTURING SYSTEM

(71) Applicant: Conopco, Inc., Englewood Cliffs, NJ (US)

(72) Inventors: Gislene Splendore Bortolai, Vila Brandina (BR); Mariangela Gomes de Oliveira Sichmann, São Paulo (BR); Erika Castanho, Campinas (BR); Lisanne Beatriz Grigolon, São Paulo (BR); Cristiane Aparecida Furtado Canto, São Paulo (BR)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 15/038,832

(22) PCT Filed: Nov. 19, 2014

(86) PCT No.: PCT/EP2014/075052
§ 371 (c)(1),
(2) Date: May 27, 2016

(87) PCT Pub. No.: WO2015/075086
PCT Pub. Date: May 28, 2015

(65) Prior Publication Data
US 2017/0049682 A1    Feb. 23, 2017

(30) Foreign Application Priority Data
Nov. 25, 2013  (EP) ................................. 13194326

(51) Int. Cl.
*A61K 8/86*  (2006.01)
*A61K 8/36*  (2006.01)
(Continued)

(52) U.S. Cl.
CPC .............. *A61K 8/86* (2013.01); *A61K 8/0216* (2013.01); *A61K 8/0241* (2013.01); *A61K 8/29* (2013.01);
(Continued)

(58) Field of Classification Search
None
See application file for complete search history.

(56) References Cited

U.S. PATENT DOCUMENTS 4,185,086 A * 1/1980 Zeitz .................... A61K 8/25
                                                    424/69
5,786,312 A * 7/1998 Post ..................... C11D 17/006
                                                    510/152
(Continued)

FOREIGN PATENT DOCUMENTS

EP    0222525    5/1987
FR    2552099    3/1985
(Continued)

OTHER PUBLICATIONS

Search Report in EP13194326, dated Apr. 28, 2014, EP.
(Continued)

*Primary Examiner* — Ernst V Arnold
*Assistant Examiner* — Kyung Sook Chang
(74) *Attorney, Agent, or Firm* — Ronald A. Koatz (57) ABSTRACT

The invention relates to bars which provide specific combinations and amounts of nonionic polymer, polyol, short chain fatty acid and solid particles. These specific combinations provide both improved sensory and improved fragrance delivery.

10 Claims, 1 Drawing Sheet

(51) Int. Cl.
*C11D 9/26* (2006.01)
*A61Q 19/10* (2006.01)
*A61K 8/29* (2006.01)
*A61K 8/02* (2006.01)
*C11D 9/18* (2006.01)
*C11D 9/22* (2006.01)
*C11D 9/48* (2006.01)
*A61K 8/34* (2006.01)
*C11D 9/44* (2006.01)

(52) U.S. Cl.
CPC .............. *A61K 8/345* (2013.01); *A61K 8/361* (2013.01); *A61Q 19/10* (2013.01); *C11D 9/18* (2013.01); *C11D 9/225* (2013.01); *C11D 9/26* (2013.01); *C11D 9/265* (2013.01); *C11D 9/442* (2013.01); *C11D 9/48* (2013.01); *A61K 2800/592* (2013.01)

(56) References Cited

U.S. PATENT DOCUMENTS 6,706,675 B1  3/2004  Demson et al.
7,838,480 B2 * 11/2010  Sidwa .................... C11D 13/14
                                                            510/141

FOREIGN PATENT DOCUMENTS

| GB | 2001098 | 1/1979 |
| WO | WO0180820 | 11/2001 |
| WO | WO0180821 | 11/2001 |
| WO | WO2006015149 | 2/2006 |
| WO | WO2013076047 | 5/2013 |

OTHER PUBLICATIONS

Search Report in PCTEP2014075052, dated Jan. 15, 2015.
Written Opinion 2 in PCTEP2014075052, dated Dec. 7, 2015.
Written Opinion in PCTEP2014075052, dated Jan. 15, 2015.

* cited by examiner

SOAP BAR FORMULATIONS WITH IMPROVED SKIN SOFTNESS COMPRISING NONIONIC POLYMER STRUCTURING SYSTEM

FIELD OF THE INVENTION

The invention relates soap bar formulations with improved skin softness comprising nonionic polymer structuring system and which are suitable for the mass market. The soap bars include a nonionic polymer structuring system, polyols and short chain free fatty acids. Typically, the bars of the present invention are not translucent, which means they usually do not allow light to pass through them; they are not, however transparent, especially due to the presence of solid particle materials. Further, the bar compositions of the invention are capable of being manufactured at high production rates by processes that generally involve extrusion to form ingots or billets, and stamping or molding of these billets into individual tablets, cakes, or bars. By the term "capable of high manufacturing rates" is meant that the soap bar mass is capable of being extruded at a rate in excess of 9 kg per minute, preferably at or exceeding 27 kg per minute and ideally at or exceeding 36 kg per minute. Personal washing bars produced from compositions according to the invention, in addition to being capable of being processed at high production rates, also possess a range of desirable physical properties that make them highly suitable for every day use by mass market consumers.

BACKGROUND OF THE INVENTION

Personal washing bars such as soap bars have played an important role in hygiene and their routine use has been critical in reducing the spread of communicable diseases. Manufacturers have continuously sought ways to improve the in-use sensory properties and skin compatibility of personal washing bars and to increase their affordability to consumers around the world.

Fatty acid soaps derived from triglycerides still remain the predominant surfactant used in the majority of personal wash bars. The main benefit of such soap bars is their cleaning capacity. Nonetheless consumers perceive other benefits such as amount of lather, thickness of lather, rate of lather formation, speed of rinsing, rate of wear of the soap bar, consistency of the bar, formation of mush, delivery of fragrance and softness of the skin after use.

Consumers around the world view the provision of soft skin after use and delivery of fragrance as key attributes to high quality soap bars. One strategy that has been used to deliver such attributes is the use of synthetic surfactants. Use of high levels of synthetic surfactants, however, can lead to various negative properties. These include significant formation of mush, accelerated rate of wear of the bar during use, and decreased speed of rinsing.

As noted, consumers also desire to improve the delivery of fragrance. This approach usually relies upon increased charges of fragrance in the soap bar composition. Use of high levels of perfume or fragrance can be extremely expensive, especially when compared with the rest of the soap bar ingredients. Additionally, even though higher amounts of fragrance are used, there is often a huge loss of fragrance during storage due, for example, to evaporation of the fragrance.

Examples of approaches based on the above concepts include:

U.S. Pat. No. 6,706,675 discloses a translucent soap bar composition that includes a soap mixture, a polyalkylene glycol, at least one of glycerin and sorbitol, water and optionally, free fatty acid. The soap bar composition exhibits translucent properties. Bars of the subject invention contain less polyethylene glycol (PEG) and the molecular weight of the PEG is typically higher than used in this reference. Larger amounts appear to be required in the reference to create greater translucency (column 6, lines 38-41).

WO 13/076047 discloses soap bars having improved lathering effect by limiting the amounts of myristic acid and using specifically defined ratios of fatty acids.

WO 01/80820 discloses a method for cleansing skin comprising washing with bars comprising predominantly fatty acid soap; free fatty acid and polyalkylene glycol in defined ratios, wherein skin condition is improved as measured by reduced skin damage.

WO 01/80821 discloses bars comprising fatty acid soaps, free fatty acid, polyalkylene glycol and specific salts of protic acid and a process for making the bars.

Further extensive experimentation has revealed that the increased skin softness properties of compositions structured with nonionic polymers combined with short chain free fatty acids and polyols such as glycerol and solid particles is surprisingly related to the levels and relative proportions of such ingredients which are present in the soap mixture.

It was surprisingly found that the combination of specific ranges of percentages by weight of nonionic polymers, (e.g., Polyox WSR-N60K); polyols; short chain free fatty acid (e.g., fatty acids between ten and fourteen carbons); and solid particles were key parameters in delivering improved softness to the skin combined with superior delivery of fragrance. This understanding has now allowed the definition of a composition space for soap bars having a much better delivery of attributes in a narrow range of ingredients, e.g., 0.01-1% of nonionic polymers, 0.1-20% of polyols, 0.01-5% of free fatty acids having lower carbon chain, and 0.1-10% of solid particles, which bars have highly acceptable in-use properties and can be manufactured by high speed extrusion. This technology is the subject of the present invention.

SUMMARY OF THE INVENTION

The personal washing bars of the invention are preferably extruded and preferably stamped bars suitable for mass market applications. One embodiment of the invention is a personal washing bar comprising:
a. at least 40% by weight, preferably 60 to 90% by weight soap;
b. from 0.01% to 1% by weight of a nonionic polymer;
c. from 0.1 to 20% by weight of a polyol,
d. from 0.01 to 5%, preferably 0.1 to 2.5% by weight of free fatty acid with lower carbon chain (e.g., carbon chain length $C_{14}$ and below, most preferably $C_{12}$,
e. from 0.1 to 10% by weight of solid particles,
f. the remainder of water In a preferred embodiment, the nonionic polymer is polyethylene glycol and its molecular weight lies within a range of 80,000 to about 8,000,000 Daltons. Specifically, the molecular weight of the polyethylene glycol component is 2,000,000 Daltons.

This and other embodiments are described more fully below in the following written description and various embodiments that are illustrated in the examples.

DETAILED DESCRIPTION OF THE INVENTION

As used herein % or wt % refers to percent by weight of an ingredient as compared to the total weight of the composition or component that is being discussed (generally the composition of the soap bar or the composition of the fatty acid soap).

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified. Unless otherwise specified the term composition will refer to the composition of the continuous phase of the bar.

For the avoidance of doubt the word "comprising" is intended to mean "including" but not necessarily "consisting of" or "composed of." In other words, the listed steps, options, or alternatives need not be exhaustive.

The present invention relates to personal washing bars having at least 40% by wt. soap in which the composition of the bar further comprises 0.01 to 1% nonionic polymers; 0.01% to about 20% of a polyol; from 0.01 to 5% by weight of free fatty acid with lower carbon chain; and from about 0.01% to about 10% of solid particles. The compositions used to prepare the bars of the invention and the methods used to manufacture and evaluate the compositions and bars made from the compositions are described below.

The term "skin softness" is used in a broad sense to describe the art into which various properties of the skin may be present. The "skin softness" is ultimately defined by user experience and is a benefit substantially consistent across cultures. The "skin softness" generally comprises the perception of consumers about the feel of skin. This perception is usually related to skin feel in three stages: during use, immediately post use and delayed post use. In the present application, skin softness comprises the sensory experience evaluated related to the two stages of post use skin feel. Consumers around the world have different perceptions about the meaning of skin softness, but in general, consumers describe this benefit as skin smoothness and silkiness and it is described as the opposite feeling of skin dryness.

The bar compositions of the present invention are capable of delivering a combination of skin softness and superior delivery of fragrance.

Personal washing bars produced from compositions according to the invention, in addition to being capable of delivering skin softness and superior delivery of fragrance, also possess good levels of other properties highly desired by consumers. This includes rate of wear, less formation of mush, and consistency and speed of rinsing and make the bars highly suitable for every day use by mass market consumers.

Composition of the Soap Bar
Fatty Acid Soap

The fatty acid soaps, optional surfactants and all the components of the bar should be suitable for routine contact with human skin and preferably yield bars that are high lathering.

The preferred type of surfactant is fatty acid soap. The term "soap" is used herein to mean an alkali metal or alkanol ammonium salts of aliphatic, alkane-, or alkene monocarboxylic acids usually derived from natural triglycerides. Sodium, potassium, magnesium, mono-, di- and tri-ethanol ammonium cations, or combinations thereof, are the most suitable for purposes of this invention. In general, sodium soaps are used in the compositions of the invention, but from about 1% to about 25% of the soap may be potassium, magnesium or triethanolamine soaps. The soaps useful herein are the well known alkali metal salts of natural or synthetic aliphatic (alkanoic or alkenoic) acids having about 8 to about 22 carbon atoms, preferably about 10 to about 18 carbon atoms. They may be described as alkali metal carboxylates of saturated or unsaturated hydrocarbons having about 8 to about 22 carbon atoms.

Soaps having the fatty acid distribution of coconut oil and palm kernel oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available triglyceride fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12 to 18 carbon atoms.

The preferred soaps for use in the present invention should include at least about 20% saturated soaps, i.e., soaps derived from saturated fatty acids, preferably at least about 40% saturated soaps by weight of the soap.

Soaps can be classified into three broad categories which differ in the chain length of the hydrocarbon chain, i.e., the chain length of the fatty acid, and whether the fatty acid is saturated or unsaturated. For purposes of the present invention these classifications are:

Lauric soaps encompass soaps which are derived predominantly from $C_{12}$ to $C_{14}$ saturated fatty acid, i.e. lauric and myristic acid, but can contain minor amounts of soaps derived from shorter chain fatty acids, e.g., $C_{10}$. Lauric soaps are generally derived in practice from the hydrolysis of nut oils such as coconut oil and palm kernel oil.

Stearic soaps encompass soaps which are derived predominantly from $C_{16}$ to $C_{18}$ saturated fatty acid, i.e. palmitic and stearic acid but can contain minor level of saturated soaps derived from longer chain fatty acids, e.g., $C_{20}$. Stearic soaps are generally derived in practice from triglyceride oils such as tallow, palm oil and palm stearin.

Oleic soaps encompass soaps which are derived from unsaturated fatty acids including predominantly oleic acid ($C_{18:1}$), linoeleic acid ($C_{18:2}$), myristoleic acid ($C_{14:1}$) and palmitoleic acid ($C_{16:1}$) as well as minor amounts of longer and shorter chain unsaturated and polyunsaturated fatty acids. Oleic soaps are generally derived in practice from the hydrolysis various triglyceride oils and fats such as tallow, palm oil, sunflower seed oil and soybean oil.

Coconut oil employed for the soap may be substituted in whole or in part by other "high-lauric" or "lauric rich" oils, that is, oils or fats wherein at least 45% of the total fatty acids are composed of lauric acid, myristic acid and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

While not wishing to be bound by theory, it is believed that, when a solid mass which comprises a mixture of lauric, stearic and oleic soaps is heated, the lauric and oleic soaps, which are more water soluble and have lower melting points than stearic soaps, combine with water and other components present in the composition to form a more or less fluid liquid crystal phase depending on water content and temperature. This transformation of lauric and oleic soaps from a solid to a liquid crystal phase provides plasticity to the mass which allows it to be mixed and worked under shear, i.e. the mass is thermoplastic.

A preferred soap is a mixture of about 10% to about 40% derived from coconut oil, palm kernel oil or other laurics rich oils and about 90% to about 60% tallow, palm oil, palm stearin or other stearics rich oils or a combination thereof provided the ratio of oleics and laurics soaps, $R_{OL}$, satisfies the above criteria.

Soaps may be made by the classic kettle boiling process or modern continuous soap manufacturing processes wherein natural fats and oils such as tallow, palm oil or coconut oil or their equivalents are saponified with an alkali metal hydroxide using procedures well known to those skilled in the art. Two broad processes are of particular commercial importance. The SAGE process where triglycerides are saponified with a base, e.g., sodium hydroxide, and the reaction products extensively treated and the glycerin component extracted and recovered. The second process is the SWING process where the saponification product is directly used with less exhaustive treatment and the glycerin from the triglyceride is not separated but rather included in the finished soap noodles and/or bars.

Alternatively, the soaps may be made by neutralizing fatty acids (e.g., distilled fatty acids), such as lauric ($C_{12}$), myristic ($C_{14}$), palmitic ($C_{16}$), stearic ($C_{18}$) and oleic acid ($C_{18:1}$) acids and their mixtures with an alkali metal hydroxide or carbonate.

Skin Softness Delivery System

The skin softness delivery system includes one or more nonionic polymer, selected from the group of nonionic polymers such as poly ethylene glycols and their mixtures; free fatty acids, preferably short chain free fatty acids; one or more polyols and solid particles material.

Nonionic Polymer

A first critical component of the skin softness delivery system is a nonionic polymer. The term "nonionic polymer" is used herein to designate materials that when present at relatively low levels (generally less than 1% based on the total weight of the bar composition) will significantly reduce the perceived friction between the wet bar and the skin, thus delivering better perceived skin softness. The nonionic polymer greatly modifies the viscosity of the soap bar and must be used sparingly, preferably at low levels, most preferably at less than 1%, especially when combined with other ingredients that also modify the rheology of the bar, such as polyols and solid particles, both further described. For instance, the preferred nonionic polymer of the present invention, Polyox WSR N-60K, have a viscosity varying from 200 to 400 centipoises (0.2 to 0.4 Pa·s) at 2% solution in water.

The most suitable nonionic polymers are useful at levels between 0.01% to about 1%, preferably from 0.05% to about 0.5% and more preferably from 0.05% to about 0.3%.

Nonionic polymers, apparently, are particularly useful in washing soap bar compositions which are made of fatty acid soaps. It has been found that the use of soap bar compositions which are made of fatty acid soaps increases the dryness of the skin and the bars are perceived as "harsh to skin" (have a high perceived level of dryness on the skin after use). Although some consumers do not mind this sensory quality, others highly dislike it. In general, consumers prefer bars that are perceived to leave a fresh and moist sensation on their skin and are perceived as being soft and gentle to the skin.

Suitable nonionic polymers include poly ethylene glycols and their mixtures thereof.

It is preferred that nonionic polymers have high molecular weight, e.g., at least about 80,000 to about 3,000,000, preferably 100,000 to about 5,000,000.

Particularly suitable nonionic polymers are high molecular weight polyethylene oxide resins. Preferably the molecular weight of the polyethylene oxide resin is greater than 80,000 Daltons, more preferably at least 100,000 Daltons and most preferably at least 400,000 Daltons. Examples of suitable high molecular weight polyethylene oxide resins are water soluble resins supplied by Dow Chemical Company under the trade name POLYOX. An example is WSR N-60K (molecular weight 2,000,000 Daltons).

Polyols

A second critical component of the skin softness delivery system is a polyol or mixture of polyols. Polyol is a term used herein to designate a compound having multiple hydroxyl groups (at least two, preferably at least three) which is highly water soluble, preferably freely soluble, in water.

Many types of polyols are available including: relatively low molecular weight short chain polyhydroxy compounds such as glycerol and propylene glycol; sugars such as sorbitol, manitol, sucrose and glucose; modified carbohydrates such as hydrolyzed starch, dextrin and maltodextrin, and polymeric synthetic polyols such as polyalkylene glycols, for example polyoxyethylene glycol (low molecular PEG) and polyoxypropylene glycol (PPG).

Preferred polyols are relatively low molecular weight compound which are either liquid or readily form stable highly concentrated aqueous solutions, e.g., greater than 50% and preferably 70% or greater by weight in water. These include low molecular weight polyols and sugars.

Especially preferred polyols are glycerol, sorbitol, PEGs and their mixtures.

The level of polyol is critical in forming a thermoplastic mass whose material properties are suitable for both high speed manufacture (27-36 Kg/min) and for use as a personal washing bar. It has been found that when the polyol level is too low, the mass is not sufficiently plastic at the extrusion temperature, typically 40° C. to 45° C. Conversely, when the polyol level is too high, the mass becomes too soft to be efficiently formed into bars by extrusion at normal process temperatures.

The level of polyol should be between 0.1% to about 20%, preferably from 1 to about 15% and most preferably from 1 to about 10% by weight of composition.

Free Fatty Acid and Triglycerides

A third critical component of the skin softness delivery system is a fatty acid and/or triglycerides which are useful for improving lather, as well as modifying the rheology at low levels incorporated in composition to increase plasticity.

Potentially suitable fatty acids are $C_8$-$C_{22}$ fatty acids. Preferred fatty acids are $C_{12}$-$C_{18}$, preferably predominantly saturated, straight-chain fatty acids. However, some unsaturated fatty acids can also be employed. Of course the free fatty acids can be mixtures of shorter chain length (e.g., $C_{10}$-$C_{14}$) and longer chain length (e.g., $C_{16}$-$C_{18}$) chain fatty acids. For example, one useful fatty acid is fatty acid derived from high-lauric triglycerides such as coconut oil, palm kernel oil, and babasu oil.

The fatty acid can be incorporated directly or they can be generated in-situ by the addition of a protic acid to the soap during processing. Examples of suitable protic acids include mineral acids such as hydrochloric acid and sulfuric acid, adipic acid, citric acid, glycolic acid, acetic acid, formic acid, fumaric acid, lactic acid, malic acid, maleic acid, succinic acid, tartaric acid and polyacrylic acid.

The level of fatty acid having chain lengths of 14 carbon atoms and below should generally not exceed about 5%, preferably not exceed about 2.5% and most preferably be about 1% or less based on the total weight of the continuous phase. A preferred short chain length fatty acid is $C_{12}$ lauric acid. Most preferably, it is used at a level of 2-3% by weight. It is especially preferred to use it in combination with 0.01 to 0.5% polyethylene glycol to provide benefits of the invention.

Solid Particles Materials

A fourth critical component of the skin softness delivery system is the presence of one or more solid particle materials. By solid particle material is meant materials that are present in the continuous phase as finely divided solid particles and are suitable for personal washing applications. The solid particle material can be inorganic or organic or a combination as long as it is substantially solid; most preferably, insoluble in water.

Preferred inorganic solid particle materials include talc and calcium carbonate. Talc is a magnesium silicate mineral material, with a sheet silicate structure represented by the chemical formula $Mg_3Si_4(O)_{10}(OH)_2$, and may be available in the hydrated form. Talc has a plate-like morphology, and is substantially oleophilic/hydrophobic.

Calcium carbonate or chalk exists in three crystal forms: calcite, aragonite and vaterite. The natural morphology of calcite is rhombohedral or cuboidal, acicular or dendritic for aragonite and spheroidal for vaterite.

Commercially, calcium carbonate or chalk (precipitated calcium carbonate) is produced by a carbonation method in which carbon dioxide gas is bubbled through an aqueous suspension of calcium hydroxide. In this process the crystal type of calcium carbonate is calcite or a mixture of calcite and aragonite.

Examples of other optional solid particle materials include alumino silicates, aluminates, silicates, silicas, phosphates, insoluble sulfates, borates and clays (e.g., kaolin, china clay) and their combinations.

Organic solid particle materials include insoluble polysaccharides such as highly crosslinked or insolubilized starch (e.g., by reaction with a hydrophobe such as octyl succinate); synthetic or natural polymers such as various polymer lattices and suspension polymers and mixtures thereof.

Suitable starch materials include natural starch (from corn, wheat, rice, potato, tapioca and the like), pregelatinzed starch, various physically and chemically modified starch and mixtures thereof. By the term natural starch is meant starch which has not been subjected to chemical or physical modification—also known as raw or native starch.

The skin softness system should be between 0.1% to about 10% of solid particles material, preferably from 0.5% to about 7% and most preferably from 1% to about 5% based on the total weight of the composition.

Preferred combinations of the composition of the soap bar are a high molecular weight polyethylene glycol (Polyox), glycerol, a free fatty acid with lower carbon chain ($C_{14}$ and below, most preferably $C_{12}$), talc and the remainder of water.

Most preferred combinations of the composition have at least 40% by weight of soap; from 0.01% to 1% by weight of a high molecular weight polyethylene glycol (Polyox); from 0.1 to 20% by weight of a polyol, preferably a glycerol, from 1 to 5% by weight of free fatty acid with lower carbon chain (especially lauric acid), from 0.1 to 10% by weight of talc and the remainder of water.

Water Content

The bar compositions of the invention do not comprise an especially high level of water compared to typical extruded and stamped soap bars which typically present no more than 30% water when freshly made, i.e., after extrusion and stamping.

It is stressed that the preferred water levels quoted above refers to freshly made bars. This quantity "initial water level" or "initial water content" of the freshly made bar" is also designated as the "nominal water content" or "nominal water level" of the composition. As is well known, soap bars are subject to drying out during storage, i.e., water evaporates from the bar when the relative humidity is lower than the partial vapor pressure of water in equilibrium with the bar composition although the amount of evaporation depends on the rate of diffusion of water from the bar. Hence, depending upon how the bar is stored (type of wrapper, temperature, humidity, air circulation, etc) the actual water content of the bar at the moment of sampling can obviously differ significantly from the nominal water content of the bar immediately after manufacture.

Optional Ingredients

Synthetic Surfactants

The bar compositions can optionally include non-soap synthetic type surfactants (detergents)—so called "syndets". Syndets can include anionic surfactants, nonionic surfactants, amphoteric or zwitterionic surfactants and cationic surfactants.

The level of synthetic surfactant present in the bar is generally not greater than about 25% in the continuous phase although inclusion of higher levels in the bar may be advantageous for some applications. Some embodiment of the invention include syndets at a levels of less than 15%, preferably less than about 7%.

Especially preferred syndets include anionic surfactants (non-soap), amphoteric surfactants and nonionic surfactants.

Advantageously, the toilet bar compositions of the present invention may contain one or more non-soap anionic syndet surfactants (simply designated "anionic syndets"). Suitable anionic syndets may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate. Alpha olefin sulfonates are another suitable anionic surfactant.

The anionic syndet may also be an alkyl sulfate (e.g., $C_{12}$-$C_{18}$ alkyl sulfate), especially a primary alcohol sulfate or an alkyl ether sulfate (including alkyl glyceryl ether sulfates).

The anionic syndet can also be a sulfonated fatty acid such as alpha sulfonated tallow fatty acid, a sulfonated fatty acid ester such as alpha sulfonated methyl tallowate or mixtures thereof.

The anionic syndet may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates or lactylates, $C_8$-$C_{22}$ monoalkyl succinates and maleates, sulphoacetates, and acyl isethionates.

Another class of anionic syndets is $C_8$ to $C_{20}$ alkyl ethoxy (1-20 EO) carboxylates.

Another suitable anionic syndet is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to carbon atoms. The acyl isethionate may also be alkoxylated isethionates Frequently, the anionic syndet will comprise a majority of the synthetic surfactants used in the composition.

Amphoteric surfactants which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a carbohydrate or sugar based, ethers, esters or amides, such as alkyl (poly)saccharides and alkyl (poly)saccharide amides.

Examples of cationic detergents are the quaternary ammonium compounds such as alkyldimethylammonium halides.

Other surfactants which may be used are described in U.S. Pat. No. 3,723,325 to Parran Jr. and "Surface Active Agents and Detergents" (Vol. I & II) by Schwartz, Perry & Berch, both of which are also incorporated into the subject application by reference.

Adjuvants

Adjuvants are ingredients that improve the aesthetic qualities of the bar especially the visual, tactile and olefactory properties either directly (perfume) or indirectly (preservatives). A wide variety of optional ingredients can be incorporated in bars of the current invention. Examples of adjuvants include but are not limited to: perfumes; opacifying agents such as fatty alcohols, ethoxylated fatty acids, solid esters, and $TiO_2$; dyes and pigments; pearlizing agent such as $TiO_2$ coated micas and other interference pigments; plate like mirror particles such as organic glitters; sensates such as menthol and ginger; preservatives such as dimethyloldimethylhydantoin (Glydant XL1000), parabens, sorbic acid and the like; anti-oxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; and mixtures thereof. Preferably, the bars of the present invention comprise perfume and/or fragrance.

The level of pearlizing agent should be between about 0.1% to about 3%, preferably between about 0.1% and 0.5% and most preferably between about 0.2% to about 0.4% based on the total weight of the composition.

Adjuvants are commonly collectively designated as "minors" in the soap making art and frequently include at a minimum, colorant (dyes and pigments), perfume, preservatives and residual salts and oils from the soap making process, and various emotive ingredients such as witch-hazel. Minors generally constitute 0.01 to 5% by weight of the composition, preferably 0.5% to 2%.

Skin Benefit Agents

A particular class of optional ingredients highlighted here is skin benefit agents included to promote skin and hair health and condition. Potential benefit agents include but are not limited to: lipids such as cholesterol, ceramides, and pseudoceramides; antimicrobial agents such as triclosan; sunscreens such as cinnamates; exfoliant particles such as polyethylene beads, bentonites, walnut shells, apricot seeds, flower petals and seeds, and inorganics such as silica, and pumice; additional emollients (skin softening agents) such as long chain alcohols and waxes like lanolin; additional moisturizers; silicones, petroleum jelly, mineral oil, skin-toning agents; skin nutrients such as vitamins like Vitamins C, D and E and essential oils like bergamot, citrus unshiu, calamus, and the like; water soluble or insoluble extracts of avocado, grape, grape seed, myrrh, cucumber, watercress, calendula, elder flower, geranium, linden blossom, amaranth, seaweed, gingko, ginseng, carrot; impatiens balsamina, camu camu, alpina leaf and other plant extracts such as witch-hazel, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxy acids, beta hydroxy acids, e.g. salicylic acid and derivatives thereof; skin soothing agents such as aloe vera, jojoba oil, propionic and acetic acid derivatives, fenamic acid derivatives; artificial tanning agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth)acrylic acid and a hydrophobic monomer comprised of long chain alkyl (meth) acrylates; anti-itch agents such as hydrocortisone, methdilizine and trimeprazine hair growth inhibition; 5-alpha reductase inhibitors; agents that enhance desquamation; antiglycation agents; anti-dandruf agents such as zinc pyridinethione; hair growth promoters such as finasteride, minoxidil, vitamin D analogues and retinoic acid and mixtures thereof.

Soap bar formulations were evaluated by internal and external trained panelists and by instrumental analysis. The results are shown below.

EXAMPLES

The following non-limiting examples illustrate various aspects of the invention and preferred embodiments. Examples of the invention are designated as "E" while comparative examples are designated as "C".

Only the compositions E1, E2 and E3 have significant results versus reference regarding soft skin benefits without compromising in use attributes.

The soap bar formulations (References 1, and 3, Examples E1, E2 and E3, Comparative examples C1 to C8) were evaluated by internal and external trained panelists to provide consumer impressions, based in attributes from Chart 1. The soap bar formulations were tested with consumers in Brazil, India and South Africa in a Home in Use Comparative Proto-monadic and blind test (7 days of usage period).

CHART 1

| | |
|---|---|
| 1 | Makes my skin feeling soft and smooth |
| 2 | Giving skin a squeaky clean feel |
| 3 | Is gentle to my skin |
| 4 | Is suitable for the whole family |
| 5 | Leaves my skin feeling moisturized |
| 6 | The bar lasts a long time (yields in terms of translations) |
| 7 | Soap does not get soggy/mushy |
| 8 | Does not dry out my skin |
| 9 | It does not crack |
| 10 | Does not leave skin tight |
| 11 | Easy to rinse off |
| 12 | Produces the right amount of lather |
| 13 | Has a long lasting fragrance |
| 14 | Lathers easily/Speed of lathering |
| 15 | Ease of holding the soap on hands |
| 16 | It does not dissolve or melt quickly during use |
| 17 | It does not leave my skin sticky |
| 18 | It does not leave residue on my skin |
| 19 | It forms moisturizing film on the skin |
| 20 | It leaves my skin fresh |
| 21 | It makes my skin feel velvety |
| 22 | It hydrates my skin |
| 23 | It conditions my skin |
| 24 | It gives a visibly soft and smooth skin |
| 25 | It gives a long lasting soft and smooth skin |
| 26 | Makes my skin soft and smooth after use |
| 27 | I don't feel the need to use a moisturizer |
| 28 | Not being harsh/irritating to the skin |
| 29 | Has a pleasant fragrance |
| 30 | Produces a rich, creamy lather |
| 31 | It is effective in removing germs |
| 32 | It has the consistency that I like |
| 32 | It is a high quality product |

The results were inputted in the statistical software Minitab Version 15 and the attributes that presented significant results at 95% confidence level for the ranges of the ingredients studied are shown in the tables below, in a visual fashion.

TABLE 1

Compositions of reference, example and comparative examples. Summary of first Consumer Test results

| | Reference 1 | E1 | C1 | C2 | С3 |
|---|---|---|---|---|---|
| Fat Charge | 80/20 SAGE Tallow | 90/10 SAGE Tallow | 70/30 SAGE Tallow | 90/10 SAGE Tallow | 80/20 SAGE Tallow |
| Sodium Anhydrous Soap | 77.68 | 80.93 | 72.53 | 78.53 | 80.53 |
| Water | 14.00 | 12.50 | 13.50 | 14.00 | 14.00 |
| Glycerol | 3.00 | 1.15 | 1.15 | 1.15 | 1.15 |
| Titanium Dioxide | 0.50 | 0.50 | 0.50 | 0.50 | 0.50 |
| Lauric Acid | | 3.50 | | | |
| Polyox WSR N-60K[1] | | 0.10 | | | |
| Red Pigment CI 12490 | 0.0044 | 0.0044 | 0.0044 | 0.0044 | 0.0044 |
| Sunflower Oil | 0.50 | | 0.50 | 0.50 | 0.50 |
| Talc | | 1.00 | | | |
| EDTA | 0.03 | 0.03 | 0.03 | 0.03 | 0.03 |
| EHDP | 0.04 | 0.04 | 0.04 | 0.04 | 0.04 |
| Calcium Carbonate | 3.00 | | 10.00 | 2.00 | 2.00 |
| Sodium Carbonate | | | 0.50 | | |
| Silicone | | | | 2.00 | |
| Perfume | 1.25 | 1.25 | 1.25 | 1.25 | 1.25 |
| Summary of Consumer Test Results | — | Significant better than reference in several attributes of soft skin benefit* | Parity to reference on soft skin benefit | Parity to reference on soft skin benefit | Parity to reference on soft skin benefit |

[1]Polyox WSR N-60K is a water soluble resin which has INCI (International Nomenclature of Cosmetic Ingredients) name of PEG-45M, an approximate molecular weight (according to Dow ® Company product brochure) of about 2,000,000 and viscosity of 200 to 400 centipoise (cPs) (0.2 to 0.4 Pa · s).

As stated, "attributes of soft skin benefit" comprise an overall improved skin feeling of skin, smoothness, non-dry neither tightness of the skin.

TABLE 2

Compositions of reference, example and comparative examples.
Summary of second Consumer Test results

| | Reference 2 | E2 | C4 | C5 | C6 |
|---|---|---|---|---|---|
| Fat Charge | 80/20 DFA Vegetal | 80/20 DFA Vegetal | 80/20 DFA Vegetal | 70/30 DFA Vegetal | 80/20 DFA Vegetal |
| Sodium Anhydrous Soap | 83.51 | 81.11 | 82.01 | 83.46 | 82.56 |
| Water | 13.50 | 12.50 | 14.00 | 13.50 | 14.00 |
| Glycerol | 0.20 | 1.00 | 0.20 | 0.40 | 0.20 |
| Titanium Dioxide | 0.50 | 0.50 | 0.50 | 0.50 | 0.50 |
| Lauric Acid | | 3.50 | | | |
| Polyox WSR N-60K | | 0.10 | | | |
| CBS | 0.03 | 0.03 | 0.03 | 0.03 | 0.03 |
| Menthol | | | | | 0.45 |
| Talc | 1.00 | 1.00 | | 1.00 | 1.00 |
| EDTA | 0.04 | 0.04 | 0.04 | 0.04 | 0.04 |
| EHDP | 0.02 | 0.02 | 0.02 | 0.02 | 0.02 |
| Silicone | | | 2.00 | | |
| Free Fatty Acid | | | | | |
| Perfume | 1.20 | 1.20 | 1.20 | 1.05 | 1.20 |
| Summary of Consumer Test Results | — | Significant better than reference on soft skin benefit | Weakness versus reference on soft skin benefit | Weakness versus reference on soft skin benefit | Weakness versus reference on soft skin benefit |

TABLE 3

Compositions of reference, example and comparative examples.
Summary of third Consumer Test results

| | Reference 3 | E3 | C7 | C8 |
|---|---|---|---|---|
| Fat Charge | 85/15 Tallow SWING | 85/15 Tallow SWING | 85/15 Tallow SWING | 70/30 Tallow SWING |
| Sodium Anhydrous Soap | 69.16 | 72.56 | 72.16 | 74.16 |
| Water | 15.00 | 14.00 | 15.00 | 15.00 |
| Glycerol | 8.00 | 8.00 | 8.00 | 8.00 |
| Titanium Dioxide | 0.50 | 0.50 | 0.50 | 0.50 |
| Lauric Acid | | 3.50 | | |
| Polyox WSR N-60K | | 0.10 | | |
| CBS | 0.03 | 0.03 | 0.03 | 0.03 |
| Free Fatty Acid | 1.00 | | 1.00 | 1.00 |
| Talc | | 1.00 | | |
| EDTA | 0.04 | 0.04 | 0.04 | 0.04 |
| EHDP | 0.02 | 0.02 | 0.02 | 0.02 |
| Starch | 5.00 | | | |
| Silicone | | | | 2.00 |
| Perfume | 1.25 | 1.25 | 1.25 | 1.25 |
| Summary of Consumer Test Results | — | Significant better than reference on soft skin benefit. | Weakness versus reference on soft skin benefit. | Weakness versus reference on soft skin benefit. |

Benefit of Long Lasting Fragrance

Positive mentions for fragrance long lasting attributes for E4 were observed and attributed to the formulation. Also, spontaneous mention from fragrance house evaluation about E4 long lasting quality compared to benchmarking prototype were noted.

The prototypes were evaluated sensorially and analytically, using as protocols: external Expert Panel, external Comparative Panel external Trained Panel and CGHS internal analysis. The results are shown below.

Expert Panel

Expert Fragrance Panel objective was to assess the attributes of long lasting fragrance intensity of bar soaps over time zero to 4 hours. Evaluation occurred every thirty minutes. All the assessments were performed by trained assessors using Labeled Magnitude Scale (LMS).

In prior screening from external expert panel, mineral ingredients applied separately did not reach the same fragrance boost than when they were applied into E4 composition. Soap bars formulations with talc enabled fragrance long lasting, however E4 performed significantly better than reference. The compositions and summary of expert panel results are described in Table 4. Scores from Expert Panel are in Table 5.

TABLE 4

Compositions tested in Expert Panel

| | Reference* | E4* |
|---|---|---|
| Composition (key ingredients) | 80/20 SWING vegetal 7.0% glycerin + 2.0% talc + 21.0% water + 1.0% fragrance | 80/20 SWING vegetal 7.0% glyc. + 21.0% water + 1.0% talc + 3.5% lauric acid + 0.1% Polyox WSR N60K + 1.0% fragrance |
| Summary of Expert Panel Results | — | Superior result for long lasting fragrance attribute than reference in 90, 120 and after 150 minutes of evaluation |

*The amount of sodium anhydrous soap is 100% minus all other components. Thus, for E4, this would be 100% minus 26.6% or 73.4%. The same is true for soap on compositions of Tables 6 and 7.

TABLE 5

Scores from Expert Panel from zero to 150 minutes

| Product | T zero | | T 30 minutes | | T 60 minutes | |
|---|---|---|---|---|---|---|
| | Mean | S.D. | Mean | S.D. | Mean | S.D. |
| E4 | 5.12 | 0.41 | 4.13 | 0.33 | 3.51 | 0.50 |
| Reference | 5.13 | 0.47 | 4.02 | 0.44 | 3.49 | 0.52 |
| P-value | 0.0099 ** | | 0.0080 ** | | <0.0001 *** | |

TABLE 5-continued

Scores from Expert Panel from zero to 150 minutes

| Product | T 90 minutes | | T 120 minutes | | T 150 minutes | |
|---|---|---|---|---|---|---|
| | Mean | S.D. | Mean | S.D. | Mean | S.D. |
| E4 | 3.21 | 0.48 | 2.87 | 0.40 | 2.62 | 0.38 |
| Reference | 3.06 | 0.42 | 2.83 | 0.42 | 2.42 | 0.32 |
| P-value | <0.0001 *** | | 0.0007 *** | | 0.0038 ** | |

*** significance level of 0.1%;
** significance level of 1%;
* significance level of 5%.
Means followed by the same letter, in each column, do not differ significantly from each other at the 5% significance level (LSD test).

E4 could improve long lasting intensity scores significantly higher than reference until 150 minutes in Expert Fragrance Panels. Also the benefits were noted in Comparative Panel (please see the next topic).

E4 has shown significantly superior long lasting performance for all tested fragrances. Therefore the technology was selected as not fragrance dependent.

Consumer Comparative Panel

Consumer Comparative Panel test objective was to evaluate the fragrance substantivity on skin up to 2 hours of long lasting thorough a comparative test among different formulations assessed in pairs at T0, T30, T60, T90 and T120 min. The action standard for this consumer test is fragrance intensity of E5, E6, E7 and E8 compositions superior than references.

Long lasting superiority of E5, E6, E7 and E8 compositions was achieved for the fragrance tested. The compositions tested in Consumer panel and summary of results are shown in Tables 6 and 7.

TABLE 6

Compositions tested in Comparative Panel

| | Reference | E5 | E6 |
|---|---|---|---|
| Composition (key ingredients) | 90/10 SAGE tallow + 10.0% solid particles + 2.5% Polyol + 16.0 water + 1.1% Fragrance | 90/10 SAGE tallow + 2.5% glycerin + 16% water + 1.5% talc + 3.5% lauric acid + 0.07% Polyox WSR N60K + 1.1% Fragrance | 90/10 SWING tallow + 7.0% Glycerin + 0.05% Polyox WSR N-60K + 3.5% Lauric Acid + 1.5% Talc + 16.0% water + 1.1% Fragrance |
| Summary of Comparative Panel Results | — | Superior result for long lasting fragrance attribute than reference in all times evaluated | Superior result for long lasting fragrance attribute than reference in all times evaluated |

TABLE 7

Compositions tested in Comparative Panel

| | Reference | E7 | E8 |
|---|---|---|---|
| Composition | 80/20 SAGE vegetal + 17.5% water + 6.0% Glycerin + 0.5% Fatty Acid + 1.0 Fragrance | 80/20 SAGE vegetal + 0.07% Polyox WSR N-60K + 3.5% Lauric Acid + 1.5% Talc + 16.0% water + 2.5% Glycerin + 1.0% Fragrance | 80/20 SWING vegetal + 0.05% Polyox WSR N-60K + 3.5% Lauric Acid + 1.5% Talc + 16.0% H2O + 7.0% Glycerin + 1.0% Fragrance |
| Summary of Comparative Panel Results | — | Superior result for long lasting fragrance attribute than reference after 30, 60, 90 and 120 minutes of evaluation. | Superior result for long lasting fragrance attribute than reference in all timings evaluated. |

VitroSKin/PCA

VitroSkin is an artificial skin that mimics a skin surface and it was used in analytical tests via GCMS (gas chromatography-mass spectrometry). The methodology of soap bars application on VitroSkin simulates the use by consumers. Volatilized fragrance in a vial space was extracted via chromatograph methods, after a setting time due to long lasting in skin simulation. Data compressed were treated through Multivariate Analysis in order to find significant differences between data of chromatograms.

Figure 1:
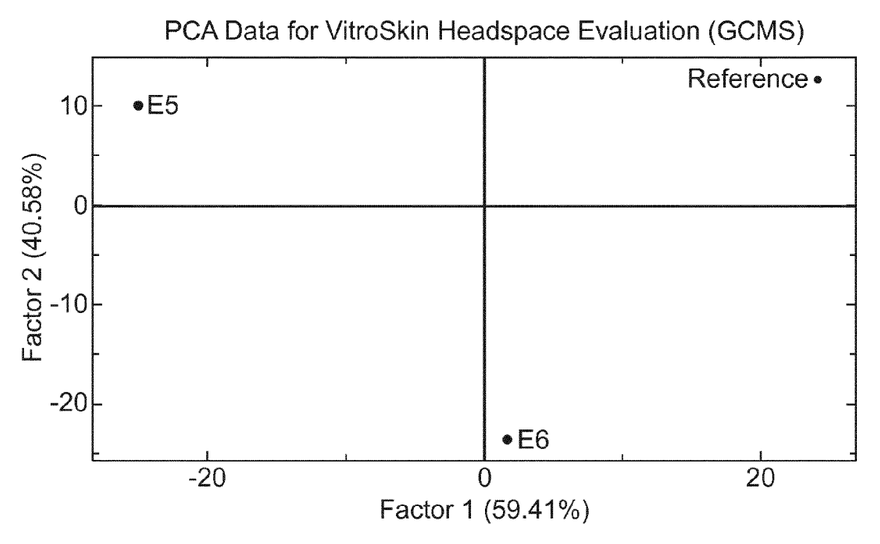
FIG. 1 provides GCMS data measured on Vitroskin (an artificial skin) indicating greater intensity of perfume burst (measured using headspace evaluation) from bars of the invention relative to comparative bar.

Considering GCMS data there was evidence that E5 and E6 compositions were consistently more intense than reference as presented in FIG. 1. For the other compositions (E7 and E8), the same consistently difference was obtained.

The invention claimed is:
1. A personal washing bar comprising:
 a. at least 40% by weight of soap;
 b. from 0.01% to 0.3% by weight of a nonionic polymer, wherein the nonionic polymer is polyethylene glycol with a molecular weight within a range of about 2,000,000 to 8,000,000 Daltons;
c. from 0.1 to 20% by weight of a polyol;
d. from 0.1 to 5% by weight of free fatty acids that are selected from the group consisting of C10-14 fatty acids, C16-18 fatty acids, and mixtures thereof;
e. from 0.1 to 10% by weight of solid particles; and
f. the remainder of water.

2. A personal washing bar according to claim 1, wherein the nonionic polymers range from 0.05% to 0.3% by weight based on the total weight of the composition.

3. A personal washing bar according to claim 1, wherein the polyol ranges from 1% to 15% by weight based on the total weight of the composition.

4. A personal washing bar according to claim 1, wherein the polyol is selected from the group consisting of glycerol, sorbitol, and their mixtures.

5. A personal washing bar according to claim 1, wherein the free fatty acid ranges from 0.1% to 2.5% by weight based on the total weight of the composition.

6. A personal washing bar according to claim 1, wherein the free fatty acids is lauric (C12) fatty acids.

7. A personal washing bar according to claim 1 wherein the solid particles range from 0.5% to 7% by weight based on the total weight of the composition.

8. A personal washing bar according to claim 1 comprising solid particles selected from the group consisting of talc, magnesium silicate, calcium carbonate, alumino silicates, aluminates, silicates, silicas, phosphates, insoluble sulfates, borates and clays, highly crosslinked or insolubilized starch, synthetic or natural polymers, natural starch, pregelatinized starch, various physically and chemically modified starch and mixtures thereof.

9. A personal washing bar according to claim 1, having enhanced long lasting perfume or fragrance intensity score compared to bars with mineral ingredients applied separately as measured by expert panel.

10. A personal washing bar according to claim 1, comprising:
a. 60 to 90% by weight soap;
b. 0.1 to 0.3% by weight polyethylene glycol;
c. 0.1 to 10% by weight glycerol;
d. 0.1 to 5% by weight lauric acid;
e. 0.1 to 3% by weight talc; and
f. remainder water wherein said bar has a soft skin benefit, which is experienced by consumers through the smooth and mild feel of the skin after product use, relative to a reference bar identical to the bar above except that it has no polyethylene glycol and no lauric acid, and wherein said bar has enhanced fragrance retention relative to a reference bar identical to the bar above except that it has no polyethylene glycol and no lauric acid.

* * * * *